United States Patent [19]

Lombardino et al.

[11] Patent Number: 4,829,062
[45] Date of Patent: May 9, 1989

[54] BENZOTHIAZINE DIOXIDE DERIVATIVES

[75] Inventors: Joseph G. Lombardino, Niantic; Anthony Marfat, Groton, both of Conn.

[73] Assignee: Pfizer Inc., New York, N.Y.

[21] Appl. No.: 154,245

[22] PCT Filed: May 16, 1986

[86] PCT No.: PCT/US86/01048
§ 371 Date: Dec. 22, 1987
§ 102(e) Date: Dec. 22, 1987

[87] PCT Pub. No.: WO87/06933
PCT Pub. Date: Nov. 19, 1987

[51] Int. Cl.[4] ............... C07D 279/02; C07D 401/12; C07D 417/12; A61K 31/54
[52] U.S. Cl. ........................... 514/226.5; 544/49
[58] Field of Search ................ 544/49; 514/226.5

[56] References Cited

U.S. PATENT DOCUMENTS

| 3,591,584 | 7/1971 | Lombardino | 260/243 |
|---|---|---|---|
| 3,787,324 | 1/1974 | Zinnes et al. | 260/243 |
| 3,822,258 | 7/1984 | Zinnes et al. | 260/243 R |
| 3,892,740 | 7/1975 | Lombardino | 260/243 R |
| 4,309,427 | 1/1981 | Lombardino | 424/246 |
| 4,551,452 | 11/1985 | Marfat | 514/222 |

OTHER PUBLICATIONS

J. G. Lombardino et al., "Potent Antiinflammatory N-Heterocyclic 3-Carboxamides of 4-Hydroxy-2-methyl-2H-1, 2-benzothiazine 1,1–Dioxide", *Journal of Medicinal Chemistry*, vol. 16, No. 5, p. 493 (1973).

*Primary Examiner*—John M. Ford
*Attorney, Agent, or Firm*—Peter C. Richardson; Lawrence C. Akers; Paul H. Ginsburg

[57] ABSTRACT

A series of novel oxyalkyl ether derivatives of various enolic oxicam compounds have been prepared, including certain novel enol oxyalkyl ethers of 4-hydroxy-2-methyl-N-(2-pyridinyl)-2H-1,2-benzothiazine-3-carboxamide 1,1-dioxide (piroxicam). These particular compounds are useful in theraphy as prodrug forms of the known anti-inflammatory and analgesic oxicams. Typical and preferred member compounds include 4-[3-(hydroxy)-n-propyloxy]-2-methyl-N-(2-pyridinyl)-2H-1,2-benzothiazine-3-carboxamide 1,1-dioxide, 4-[5-(hydroxy)-n-pentyloxy]-2-methyl-N-(2-pyridinyl)-2H-1,2-benzothiazine-3-carboxamide 1,1-dioxide, 4-[3-(methoxycarbonyloxy)-n-propyloxy]-2-methyl-N-(2-pyridinyl)-2H-1,2-benzothiazine-3-carboxamide 1,1-dioxide, 4-[3-(ethoxycarbonyloxy)-n-propyloxy]-2-methyl-N-(2-pyridinyl)-2H-1,2-benzothiazine-3-carboxamide 1,1-dioxide, 4-[4-(ethoxycarbonyloxy)-n-butyloxy]-2-methyl-N-(2-pyridinyl)-2H-1,2-benzothiazine-3-carboxamide 1,1-dioxide and 2-methyl-4-[3-(n-octyloxycarbonyloxy)-n-propyloxy]-N-(-2-pyridinyl)-2H-1,2-benzothiazine-3-carboxamide 1,1-dioxide. Methods for preparing these compounds from known starting material are provided.

18 Claims, No Drawings

BENZOTHIAZINE DIOXIDE DERIVATIVES

TECHNICAL FIELD

This invention relates to new and useful benzothiazine dioxide derivatives. More particularly, it is concerned with certain novel enol oxyalkyl ether derivatives of 4-hydroxy-2-methyl-N-(2-pyridinyl)-2H-1,2-benzothiazine-3-carboxamide 1,1-dioxide and several other closely-related oxicams, which are of especial value as prodrugs in view of their chemotherapeutic properties.

BACKGROUND ART

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including a new agent known as piroxicam. The latter substance is a member of a class of anti-inflammatory/analgesic N-heteroaryl-4-hydroxy-2-methyl-2H-1,2-benzothiazine-3-carboxamide 1,1-dioxides (known as oxicams) described and claimed in U.S. Pat. No. 3,591,584 and is specifically, 4-hydroxy-2-methyl-N-(2-pyridinyl)-2H-1,2-benzothiazine-3-carboxamide 1,1-dioxide. Other agents of this type are disclosed in U.S. Pat. Nos. 3,787,324, 3,822,258, 4,180,662 and 4,376,768, as well as in German Offenlegungschrift No. 2,756,113 and Published European patent application No. 138,223. In U.S. Pat. No. 4,434,164, there are specifically described and claimed the ethylenediamine, monoethanolamine and diethanolamine salts of 4-hydroxy-2-methyl-N-(2-pyridinyl)-2H-1,2-benzothiazine-3-carboxamide 1,1-dioxide, which are particularly valuable in pharmaceutical dosage forms as non-steroidal therapeutic agents for the treatment of painful inflammatory conditions, such as those caused by rheumatoid arthritis, since they are all crystalline, nonhygroscopic, rapidly-dissolving solids with high water solubility. In U.S. Pat. No. 4,309,427, there are disclosed certain novel acyl derivatives (i.e., enol esters) of 4-hydroxy-2-methyl-N-(2-pyridinyl)-2H-1,2-benzothiazine-3-carboxamide 1,1-dioxide and 4-hydroxy-2-methyl-N-(6-methyl-2-pyridinyl)-2H-1,2-benzothiazine-3-carboxamide 1,1-dioxide, which are useful as nonsteroidal therapeutic agents for alleviating various inflammatory conditions, including those of the skin, especially when given by the topical route of administration. However, in the continuing search for still more improved anti-inflammatory/analgesic agents, there is a need for anti-arthritic agents that are orally administrable and yet at the same time are less ulcerogenic than the parent oxicam compounds of the prior art.

In this connection, it is to be noted that while the prior described enolic oxicam lower alkyl ethers of U.S. Pat. No. 3,892,740 do not possess anti-inflammatory activity to any substantial degree, the more recently described anti-inflammatory oxyalkyl ethers of the enolic oxicams of U.S. Pat. No. 4,551,452 all require that the oxyalkyl moiety be restricted to —CH$_2$—O—, —CH(CH$_3$)—O— or —CH(C$_6$H$_5$)—O—. As a result, there is little or no information available about the effect of other oxyalkyl ethers in this area and particularly, about compounds like the corresponding enolic oxicam lower oxyalkyl ethers wherein the alkyl moiety is exclusively arranged in a straight chain.

DISCLOSURE OF THE INVENTION

In accordance with the present invention, it has now been found that certain novel enol straight-chain oxyalkyl ether derivatives of 4-hydroxy-2-methyl-N-(2-pyridinyl)-2H-1,2-benzothiazine-3-carboxamide 1,1-dioxide and several other closely-related known oxicams are useful in therapy as prodrug forms of the known anti-inflammatory and analgesic oxicams. Consequently, the compounds of this invention are useful in therapy as non-steroidal therapeutic agents for alleviating painful inflammatory conditions such as those caused by rheumatoid arthritis, for example. The novel compounds of this invention are of the formula:

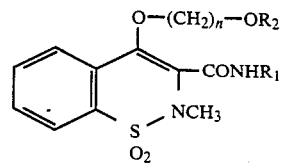

wherein R$_1$ is 2-pyridyl, 6-methyl-2-pyridyl, 6-fluoro-2-pyridyl, 6-chloro-2-pyridyl, 5-methyl-3-isoxazolyl, 2-thiazolyl, 5-methyl-2-thiazolyl, 1-oxo-2,4,6-cyclohepta-trien-2-yl, phenyl, nitrophenyl or mono- or disubstituted phenyl wherein each substituent is fluorine, chlorine, bromine, trifluoromethyl, alkyl having from one to three carbon atoms or alkoxy having from one to three carbon atoms; R$_2$ is hydrogen, alkanoyl having from two to six carbon atoms, benzoyl, p-chlorobenzoyl, toluoyl, thenoyl, furoyl, —COR$_3$ or —COOR$_3$ wherein R$_3$ is alkyl having from one to eight carbon atoms; and n is an integer from three to five.

The compounds of this invention are useful in therapy, as aforesaid, as prodrug forms of the known anti-inflammatory and analgesic oxicams from which they are derived. The term "prodrug", when used in this connection, refers to compounds which are drug precursors, which following administration and absorption in the body release the drug in vivo by some metabolic pathway or process such as hydrolysis. Accordingly, these novel compounds are particularly valuable as non-steroidal therapeutic agents for the treatment of painful inflammatory conditions, especially those caused by rheumatoid arthritis, and are particularly adapted for use in various pharmaceutical dosage forms, including those designed for oral, topical or parenteral administration. Moreover, the prodrugs of this invention are unusual in that they exhibit anti-inflammatory activity to a rather high degree in contrast to the enolic oxicam lower alkyl ethers of the aforesaid prior art (U.S. Pat. No. 3,892,740). They are also less ulcerogenic than the parent acidic oxicams from which they are derived. Accordingly, the preferred method of administration for the presently-claimed compounds is oral, although parenteral and topical formulations are also readily made available with these compounds and such formulations are found to be useful.

Of especial interest in this connection are the preferred compounds of the invention where R$_1$ in the structural formula is 2-pyridyl (i.e., derivatives of piroxicam), R$_2$ is hydrogen or —COOR$_3$ wherein R$_3$ is alkyl having from one to eight carbon atoms and n is an integer of from three to five. Typical and preferred member compounds of the invention include 4-[3-(hydroxy)-n-propyloxy]-2-methyl-N-(2-pyridinyl)-2H-1,2-benzothiazine-3-carboxamide 1,1-dioxide, 4-[5-(hydroxy)-n-pentyloxy]-2-methyl-N-(2-pyridinyl)-2-H-1,2-benzothiazine-3-carboxamide 1,1-dioxide, 4-[ 3-(methoxycarbonyloxy)-n-propyloxy]-2-methyl-N-(2-pyridinyl)-2H-1,2-benzothiazine-3-carboxamide 1,1-dioxide, 4-[3-(ethoxycarbonyloxy)-n-propyloxy]-2-methyl-N-(2-pyridinyl)-2H-1,2-benzothiazine-3-carboxamide 1,1-dioxide, 4-[4-(ethoxycarbonyloxy)-n-butyloxy]-2-methyl-N-(2-pyridinyl)-2H-1,2-benzothiazine-3-carboxamide 1,1-dioxide and 2-methyl-4-[3-(n-octyloxycarbonyloxy)-n-propyloxy]-N-(2-pyridinyl)-2H-1,2-benzothiazine-3-carboxamide 1,1-dioxide, respectively. These particular compounds are especially effective in treating many painful inflammatory conditions by the oral route of administration.

DETAILED DESCRIPTION

In the process for preparing the novel compounds of the invention, the parent oxicam compound of the formula:

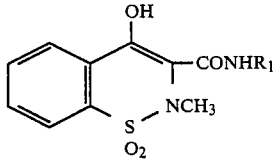

wherein $R_1$ is defined as aforesaid, is treated with at least an equivalent amount in moles of an oxyalkyl halide of the formula:

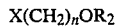

wherein $R_2$ and n are each as previously defined and X is either chlorine or bromine. This reaction is normally carried out in a reaction-inert organic solvent, preferably under substantially anhydrous conditions in the presence of at least an equivalent amount of an appropriate standard base. A particularly convenient reaction system employs acetone as the solvent and potassium carbonate as the base, with up to three or more equivalents of sodium iodide added, if desired, to enhance the rate of the reaction. It should be noted that the amount of standard base employed must be such that it is present in sufficient amount to neutralize the liberated hydrogen halide formed in the reaction. Excess of the reagent $R_2O(CH_2)_nX$ is not critical to the reaction, but such excess will generally be used in order to shift the reaction to completion in a shorter period of time. The rate of reaction will also depend greatly on the nature of X (e.g., Cl>Br) and to some extent on the nature of the $R_2O(CH_2)_n-$ group (where $R_2$ is hydrogen or an organic radical as previously defined). In general, the reaction is conducted at a temperature of from about 50° C. up to about 100° C. for a period of about 24 to about 125 hours. When acetone is employed as the solvent and potassium carbonate as the base, the reflux temperature of acetone is a particularly convenient reaction temperature for these purposes. The reaction is also conveniently followed by thin layer chromatography, thereby determining reaction times sufficient to provide complete reaction and at the same time, avoiding any unnecessary heating and excessive reaction times which can increase the level of byproduct formation and reduce yields.

The starting materials required for preparing the novel enol oxyalkyl ether derivatives of this invention are all known compounds. For instance, 4-hydroxy-2-methyl-N-(2-pyridinyl)-2H-1,2-benzothiazine-3-carboxamide 1,1-dioxide, 4-hydroxy-2-methyl-N-(6-methyl-2-pyridinyl)-2H-1,2-benzothiazine-3-carboxamide 1,1-dioxide and 4-hydroxy-2-methyl-N-(2-thiazolyl)-2H-1,2-benzothiazine-3-carboxamide 1,1-dioxide are all fully described in U.S. Pat. No. 3,591,584 to J. G. Lombardino, as well as in the paper to J. G. Lombardino et al., appearing in the *Journal of Medicinal Chemistry*, Vol. 16, p. 493 (1973), including their synthesis from readily available organic materials. The other closely-related oxicams required as starting materials in the process of this invention are readily available by methods well known to those skilled in the art, e.g., see the patent references to the other oxicams cited in the background section of the instant specification.

The oxicam prodrugs of the present invention are all readily adapted to therapeutic use as anti-inflammatory agents. For instance, 4-[3-(hydroxy)-n-propyloxy]-2-methyl-N-(2-pyridinyl)-2H-1,2-benzothiazine-3-carboxamide 1,1-dioxide, a typical and preferred agent of the present invention, exhibits anti-inflammatory activity in the standard carrageenin-induced rat foot edema test [described by C. A. Winter et al., *Proc. Soc. Exp. Biol. Med.*, Vol. 111, p. 544 (1962)], where it was found to cause a 47% inhibition in swelling at the 32 mg./kg. dose level when given by the oral route. The herein described derivatives exhibit additional advantages. For instance, they are all considerably less ulcerogenic than the parent oxicam from which they are derived. The reason for this can be best explained by the fact that after gastrointestinal absorption, the present compounds are hydrolyzed in vivo to the corresponding parent anti-inflammatory oxicam compounds. Inasmuch as the present compounds are clearly non-acidic in nature, exposure of the gastrointestinal tract to the parent acidic oxicam compounds is thereby largely minimized.

The herein described oxicam prodrugs of this invention can be administered via either the oral, parenteral or topical routes. In general, these compounds are most desirably administered in doses ranging from about 5.0 mg. up to about 1000 mg. per day, although variations will necessarily occur depending upon the weight and condition of the subject being treated and the particular route of administration chosen. However, a dosage level that is in the range of from about 0.08 mg. to about 16 mg. per kg. of body weight per day is most desirably employed. Nevertheless, variations may still occur depending upon the individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing harmful side effects provided that such higher dose levels are first divided into several small doses for administration throughout the day.

The oxicam prodrugs of this invention may be administered alone or in combination with pharmaceutically acceptable carriers by either of the three routes previously indicated. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these oxicam prodrugs in either sesame or peanut oil or in aqueous propylene glycol may be employed. The aqueous solutions should be suitably buffered (pH>8) if necessary and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid oxicam ethers topically when treating inflammatory conditions of the skin or eye and this may be preferably done by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150-190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg./kg., via the oral route of administration.

PREPARATION A

To a well-stirred solution consisting of 9.38 ml. (0.104 mole) 3-bromo-n-propanol dissolved in 25 ml. of benzene, there was added in a dropwise manner a solution of 8 ml. (0.104 mole) of methyl chloroformate in 25 ml. of benzene. The reaction mixture was then cooled to 0° C. with the aid of an ice/water bath, at which point a solution consisting of 8.3 ml. (0.104 mole) of pyridine dissolved in 25 ml. of benzene was slowly added thereto. The resulting reaction mixture was then stirred for one hour at 0° C. and for four hours at room temperature (~20° C.) while under a nitrogen atmosphere. At the end of this time, 100 ml. of diethyl ether were added to the mixture and the precipitated pyridine hydrochloride which formed was then removed from the mixture by means of filtration. The filtrate was then washed twice with 3N hydrochloric and once with brine, followed by drying over anhydrous sodium sulfate. After removal of the drying agent by means of filtration and the solvent by means of evaporation under reduced pressure, there were obtained 15.0 g. (73%) of 3-bromo-n-propyl methyl carbonate in the form of a colorless liquid. The liquid product was characterized by means of nuclear magnetic resonance data.

PREPARATION B

To a well-stirred solution consisting of 18 ml. (0.20 mole) of 3-bromo-n-propanol dissolved in 25 ml. of benzene which had been cooled to 0° C. with the aid of an ice/water bath, there was added in a dropwise manner a solution consisting of 19.1 ml. (0.20 mole) of ethyl chloroformate dissolved in 25 ml. of benzene. Upon completion of this step, the reaction mixture was treated with 19.1 ml. (0.20 mole) of pyridine which was also added in a dropwise manner. The resulting white suspension was then stirred for a period of one hour at 0° C. (while under a nitrogen atmosphere) and for six hours at room temperature. At the end of this time, the pyridine hydrochloride was removed by filtration and the organic filtrate was washed twice with 50 ml. of 3N hydrochloric acid and once with 50 ml. of brine, followed by drying over anhydrous magnesium sulfate. After removal of the drying agent by means of filtration and the solvent by means of evaporation under reduced pressure, there was obtained a colorless liquid as the residue. The latter material was subsequently stirred under a high vacuum overnight for a period of approximately 16 hours to ultimately afford 33.8 g. (80%) of 3-bromo-n-propyl ethyl carbonate (as a colorless liquid). The liquid product was characterized by means of mass spectroscopy, nuclear magnetic resonance data and infrared absorption spectra.

PREPARATION C

To a well-stirred solution consisting of 3.0 g. (0.019 mole) of 4-bromo-n-butanol dissolved in 25 ml. of benzene, there was added in a dropwise manner a solution of 1.82 ml. (0.019 mole) of ethyl chloroformate in 25 ml. of benzene. The reaction mixture was then cooled to 0° C. by means of ice/water bath, followed by the addition thereto of 1.56 ml. (0.019 mole) of pyridine dissolved in 25 ml of benzene which was added in a dropwise manner. The resulting yellow suspension was then stirred at 0° C. for a period of one hour and thereafter at room temperature for a period of four hours while under a nitrogen atmosphere. At the end of this time, 100 ml. of diethyl ether were added to the mixture and the precipitated pyridine hydrochloride which formed was then removed from the mixture by means of filtration. The organic filtrate was then washed twice with 3N hydrochloric acid and once with brine, followed by drying over anhydrous sodium sulfate. After removal of the drying agent by means of filtration and the solvent by means of evaporation under reduced pressure, there were obtained 3.38 g. (79%) of 4-bromo-n-butyl ethyl carbonate in the form of a clear colorless liquid. The liquid product was characterized by means of nuclear magnetic resonance data and infrared absorption spectra.

PREPARATION D

To a well-stirred solution consisting of 9.38 ml. (0.104 mole) of 3-bromo-n-propanol dissolved in 25 ml. of benzene which had been cooled to 0° C. with the aid of an ice/water bath, there was added in a dropwise manner a solution consisting of 20 g. (0.104 mole) n-octyl chloroformate dissolved in 25 ml of benzene. Upon completion of this step, the reaction mixture was treated with 8.3 ml. (0.104 ml.) of pyridine which was also added in a dropwise manner. The resulting white suspension was then stirred for 30 minutes at 0° C. and thereafter for a period of five hours at room temperature while under a nitrogen atmosphere. At the end of this time, 100 ml. of diethyl ether were added to the mixture and the precipitated pyridine hydrochloride was then removed by filtration. The organic filtrate was thereafter washed twice with 3N hydrochloric acid and once with brine, followed by drying over anhydrous magnesium sulfate. After removal of the drying agent by means of filtration and the solvent by means of evaporation under reduced pressure, there were obtained 26.31 g. (86%) of 3-bromo-n-propyl n-octyl carbonate in the form of a colorless liquid. The liquid product was characterized by nuclear magnetic resonance data and infrared absorption spectra.

EXAMPLE 1

A mixture consisting of 3.0 g. (0.0096 mole) of 4-hydroxy-2-methyl-N-(2-pyridinyl)-2H-1,2-benzothiazine-3-carboxamide 1,1-dioxide (prepared as described in U.S. Pat. No. 3,591,584), 2.60 g. (0.0272 mole) of 3-bromo-1-propanol and 2.50 g. (0.018 mole) of potassium carbonate in 40 ml. of acetone was refluxed for a period of three days while under a nitrogen atmosphere. At the end of this time, the solvent was removed in vacuo to yield a yellow oil/solid as the residue, which was subsequently dissolve in methylene chloride/water. The separated organic layer was then washed once with water and once with brine and finally dried over anhydrous sodium sulfate. After removal of the drying agent by means of filtration and the solvent by means of evaporation under reduced pressure, there was obtained a yellow oil as the residue (yield, ca. 5.7 g.). The latter material was subsequently chromatographed on a column of silica, using ethyl acetate/methylene chloride (1:1 by volume) as the eluant, to give 670 mg. (18%) of 4-[3-(hydroxy)-n-propyloxy]-2-methyl-N-(2-pyridinyl)-2-H-1,2-benzothiazine-3-carboxamide 1,1-dioxide in the form of a foaming white solid. Recrystallization of the solid product from isopropanol then gave 480 mg. of pale yellow-white crystals melting at 136°–137° C. The pure product was further characterized by means of mass spectroscopy, nuclear magnetic resonance data and thin layer chromotography, in addition to elemental analysis.

Anal. Calcd. for $C_{18}H_{19}N_3O_5S$: C, 55.52; H, 4.72; N, 10.79. Found: C, 55.20; H, 4.94; N, 11.06.

EXAMPLE 2

A mixture consisting of 3.0 g. (0.00906 mole) of 4-hydroxy-2-methyl-N-(2-pyridinyl)-2H-1,2-benzothiazine-3-carboxamide 1,1-dioxide, 3.33 g. (0.0272 mole) of 5-chloro-1-pentanol and 2.5 g. (0.0182 mole) of potassium carbonate in 40 ml. of acetone was refluxed for a period of one hour while under a nitrogen atmosphere. Five equivalents of sodium iodide (2.27 g.) were then added to the mixture and refluxing was continued for a period of 48 hours. At the end of this time, the solvent was removed in vacuo and the residue was taken up in methylene chloride (150 ml.)/water (150 ml.) to yield a two-phase solution system. The separated organic layer was then washed once with brine and dried over anhydrous sodium sulfate. After removal of the drying agent by means of filtration and the solvent by means of evaporation under reduced pressure, there was obtained a yellow oil as the residue. The latter material was subsequently chromatographed on a column of silica, using ethyl acetate/methylene chloride (1:1 by volume) as the eluant, to ultimately give a pure oil as product. Treatment of the oily product with toluene/hexane still gave an oil, but crystals were eventually obtained after refrigerating the latter oil for two days and then triturating same with hexane. In this way, there was ultimately obtained 1.41 g. (37%) of pure 4-[5-(hydroxy)-n-pentyloxy]-2-methyl-N-(2-pyridinyl)-2H-1,2-benzothiazine-3-carboxamide 1,1-dioxide, m.p. 111°–112° C. The pure product was further characterized by means of mass spectroscopy, nuclear magnetic resonance data, thin layer chromatography and infrared absorption spectra, in addition to elemental analysis.

Anal. Calcd. for $C_{20}H_{23}N_3O_5S$: C, 57.54; H, 5.55; N, 10.06. Found: C, 57.10; H, 5.50; N, 9.94.

EXAMPLE 3

A mixture consisting of 1.02 g. (0.00302 mole) of 4-hydroxy-2-methyl-N-(2-pyridinyl)-2H-1,2-benzothiazine-3-carboxamide 1,1-dioxide, 1.8 g. (0.00906 mole) of 3-bromo-n-propyl methyl carbonate (the product of Preparation A) and 834 mg. (0.00604 mole) of potassium carbonate in 100 ml. of acetone was refluxed for a period of 24 hours while under a nitrogen atmosphere. Three equivalents of sodium iodide (1.36 g.) and 1.8 g. of 3-bromo-n-propyl methyl carbonate were then added to the mixture and refluxing was continued for a period of 32 hours. At this point, an additional 1.36 g. of sodium iodide and 1.8 g. of 3-bromo-n-propyl methyl carbonate were added to the mixture, followed by further refluxing for a period of three days. At the end of this time, the resulting reaction mixture was cooled to room temperature (~20° C.) and then concentrated in vacuo. The residue was partitioned between water and methylene chloride, and the separated organic layer was thereafter washed twice with saturated aqueous sodium bicarbonate solution and once with brine, followed by drying over anhydrous sodium sulfate. After removal of the drying agent by means of filtration and the solvent by means of evaporation under reduced pressure, there was obtained a yellow liquid as the residue. The latter material was subsequently chromatographed on 100 g. of silica gel (0.20–0.063 mm.) and eluted with hexane/ethyl acetate to give 500 mg. (37%) of 4-[3-(methoxycarbonyloxy)-n-propyloxy]-2-methyl-N-(2-pyridinyl)-2H-1,2-benzothiazine-3-carboxamide 1,1-dioxide in the form of a colorless viscous oil. When the oily product was subjected to a high vacuum (1.0 mm. Hg) at room temperature for a period of 18 hours, crystallization occurred and there was eventually obtained 300 mg. (22%) of a pale yellow solid melting at 106°–108° C. The pure product was further characterized by means of thin layer chromatography and infrared absorption spectra, in addition to elemental analysis.

Anal. Calcd. for $C_{20}H_{21}N_3O_7S$: C, 53.68; H, 4.73; N, 9.39. Found: C, 53.04; H, 4.76; N, 9.00.

EXAMPLE 4

A mixture consisting of 1.0 g. (0.00302 mole) of 4-hydroxy-2-methyl-N-(2-pyridinyl)-2H-1,2-benzothiazine-3-carboxamide 1,1-dioxide, 1.9 g. (0.00906 mole) of 3-bromo-n-propyl ethyl carbonate (the product of Preparation B) and 834 mg. (0.00604 mole) of potassium carbonate in 100 ml. of acetone was heated to the reflux point while under a nitrogen atmosphere. Three equivalents of sodium iodide (1.36 g.) and 1.9 g. of 3-bromo-n-propyl ethyl carbonate were then added to the mixture and refluxing was contained for a period of seven hours. At this point, an additional 1.3 g. amount of sodium iodide was added to the mixture, followed by further refluxing for a period of 48 hours. The resulting mixture was then treated with an additional 1.9 g. amount of 3-bromo-n-propyl ethyl carbonate and refluxing was continued for another 24 hours. At the end of this time, the resulting reaction mixture was cooled to room temperature and then concentrated in vacuo to remove the solvent. This residue was partitioned between methylene chloride and water, and the separated organic layer was thereafter washed twice with saturated aqueous sodium bicarbonate solution and once with brine, followed by drying over anhydrous magnesium sulfate. After removal of the drying agent by means of filtration and the solvent by means of evaporation under reduced pressure, there was obtained a crude residual material. The latter material was subsequently chromatographed on 100 g. of silica gel (0.038–0.063 mm.) and eluted with methylene chloride/ethyl acetate (4:1 by volume) to give 300 mg. (22%) of pure 4-[3-(ethoxycarbonyloxy)-n-propyloxy]-2methyl-N-(2-pyridinyl)-2H-1,2-benzothiazine-3-carboxamide 1,1-dioxide (m.p. 137°–139° C.), after first being triturated with isopropyl ether and dried to constant weight. The pure white solid product was further characterized by means of mass spectroscopy, nuclear magnetic resonance data, thin layer chromatography and infrared absorption spectra, in addition to elemental analysis.

Anal. Calcd. for $C_{21}H_{23}N_3O_7S$: C, 54.65; H, 5.02; N, 9.11. Found: C, 54.25; H, 4.89; N, 8.95.

EXAMPLE 5

A mixture consisting of 1.08 g. (0.0033 mole) of 4-hydroxy-2-methyl-N-(2-pyridinyl)-2H-1,2-benzothiazine-3-carboxamide 1,1-dioxide, 2.2 g. (0.0098 mole) of 4-bromo-n-butyl ethyl carbonate (the product of Preparation C) and 8.34 mg. (0.0064 mole) of potassium carbonate in 150 ml. of acetone was refluxed for a period of 18 hours while under a nitrogen atmosphere. At this point, another 1.1 g. (0.0049 mole) of 4-bromo-n-butyl ethyl carbonate and 960 mg. (0.0064 mole) of sodium iodide were added to the mixture and refluxing was continued for a period of three days. At the end of this time, the resulting reaction mixture was cooled to room temperature and then concentrated in vacuo to remove the solvent. The residue was partitioned between methylene chloride/water, and the separated organic layer was thereafter washed twice with saturated aqueous sodium bicarbonate solution and once with brine, followed by drying over anhydrous sodium sulfate. After removal of the drying agent by means of filtration and the solvent by means of evaporation under reduced pressure, there was obtained a yellow-orange liquid as the residue. The latter material was subsequently chromatographed on 60 g. of silica gel (0.038–0.063 mm.) and eluted with methylene chloride/ethyl acetate (9:1 by volume) to give 167 mg. (10%) of pure 4-[4-(ethoxycarbonyloxy)-n-butyloxy]-2-methyl-N-(2-pyridinyl)-2H-1,2-benzothiazine-3-carboxamide 1,1-dioxide (m.p. 111°–112° C.) in the form of a white solid product. The pure product was further characterized by means of thin layer chromatography and infrared absorption spectra, in addition to elemental analysis.

Anal. Calcd. for $C_{22}H_{25}N_3O_7S$: C, 55.57; H, 5.30; N, 8.85. Found: C, 55.02; H, 5.35; N, 8.62.

EXAMPLE 6

A mixture consisting of 1.0 g. (0.00302 mole) of 4-hydroxy-2-methyl-N-(2-pyridinyl)-2H-1,2-benzothiazine-3-carboxamide 1,1-dioxide, 2.67 g. (0.00906 mole) of 3-bromo-n-propyl n-octyl carbonate (the product of Preparation D) and 834 mg. (0.00604 mole) of potassium carbonate in 100 ml. of acetone was refluxed for a period of 18 hours while under a nitrogen atmosphere. Three equivalents of sodium iodide (1.36 g.) and 2.67 g. of 3-bromo-n-propyl n-octyl carbonate were then added to the mixture and refluxing was continued for a period of 24 hours. At this point, an additional 1.36 g. of sodium iodide and 2.67 g. of 3-bromo-n-propyl n-octyl carbonate was added to the mixture, followed by further refluxing for a period of three and one-half days. At the end of this time, the resulting reaction mixture was cooled to room temperature and then concentrated in vacuo. The residue was redissolved in methylene chloride, and the resulting organic solution was thereafter washed twice with saturated aqueous sodium bicarbonate solution and once with water, followed by drying over anhydrous sodium sulfate. After removal of the drying agent by means of filtration and the solvent by means of evaporation under reduced pressure, there was obtained an orange liquid as the residue. The latter material was subsequently chromatographed on 100 g. of silica gel (0.063–0.200 mm.) and eluted with methylene chloride/ethyl acetate (4:1 by volume), followed by a further chromatograph on silica gel using hexane/ethyl acetate (1:1 by volume) as the eluant. In this way, there was eventually obtained 400 mg. (24%) of pure 2-methyl-4-[3-(n-octyloxycarbonyloxy)-n-propyloxy]-N-(2-pyridinyl)-2H-1,2-benzothiazine-3-carboxamide 1,1-dioxide in the form of a viscous yellow oil that soon solidified to a yellow solid product melting at 55°–57° C. The pure product was further characterized by means of mass spectroscopy, thin layer chromatography and infrared absorption spectra, in addition to elemental analysis.

Anal. Calcd. for $C_{27}H_{35}N_3O_7S$: C, 59.43; H, 6.47; N, 7.70. Found: C, 58.78; H, 6.26; N, 7.44.

We claim:
1. A compound of the formula:

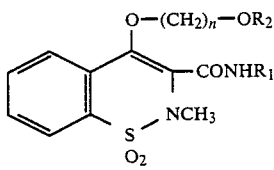

wherein
- R₁ is 2-pyridyl, 6-methyl-2-pyridyl, 6-fluoro-2-pyridyl, 6-chloro-2-pyridyl, 5-methyl-3-isoxazolyl, 2-thiazolyl, 5-methyl-2-thiazolyl, 1-oxo-2,4,6-cycloheptatrien-2-yl, phenyl, nitrophenyl or mono- or disubstituted phenyl wherein each substituent is fluorine, chlorine, bromine, trifluoromethyl, alkyl having from one to three carbon atoms or alkoxy having from one to three carbon atoms;
- R₂ is hydrogen, alkanoyl having from two to six carbon atoms, benzoyl, p-chlorobenzoyl, toluoyl, thenoyl, furoyl, —COR₃ or —COOR₃ wherein R₃ is alkyl having from one to eight carbon atoms; and
- n is an integer of from three to five.

2. A compound as claimed in claim 1 wherein R₁ is 2-pyridyl.

3. A compound as claimed in claim 1 wherein R₁ is 6-methyl-2-pyridyl.

4. A compound as claimed in claim 2 wherein R₂ is hydrogen.

5. A compound as claimed in claim 4 wherein n is three.

6. A compound as claimed in claim 4 wherein n is five.

7. A compound as claimed in claim 2 wherein R₂ is alkanoyl having from two to six carbon atoms.

8. A compound as claimed in claim 7 wherein R₂ is acetyl.

9. A compound as claimed in claim 2 wherein R₂ is benzoyl.

10. A compound as claimed in claim 2 wherein R₂ is thenoyl.

11. A compound as claimed in claim 2 wherein R₂ is furoyl.

12. A compound as claimed in claim 2 wherein R₂ is —COOR₃ wherein R₃ is alkyl having from one to eight carbon atoms.

13. A compound as claimed in claim 12 wherein R₂ is —COOCH₃ and n is three.

14. A compound as claimed in claim 12 wherein R₂ is —COOC₂H₅ and n is three.

15. A compound as claimed in claim 12 wherein R₂ is —COOC₂H₅ and n is four.

16. A compound as claimed in claim 12 wherein R₂ is —COOC₈H₁₇(n) and n is three.

17. A pharmaceutical composition comprising a pharmaceutically acceptable carrier and an effective anti-inflammatory amount of a compound as claimed in claim 1.

18. A method for treating inflammatory conditions in a warm-blooded animal, which comprises administering to said animal an effective anti-inflammatory amount of a compound as claimed in claim 1.

* * * * *